United States Patent [19]

Peake

[11] Patent Number: 4,876,285
[45] Date of Patent: Oct. 24, 1989

[54] VINYL FLUORIDES AND PESTICIDAL USES

[75] Inventor: Clinton J. Peake, Trenton, N.J.

[73] Assignee: FMC Corporation, Philadelphia, Pa.

[21] Appl. No.: 18,768

[22] Filed: Mar. 2, 1987

[51] Int. Cl.$^4$ .............................................. A01N 29/02
[52] U.S. Cl. .................................... 514/746; 514/744
[58] Field of Search ................................. 514/744, 746

[56] References Cited

U.S. PATENT DOCUMENTS

| | | | |
|---|---|---|---|
| 2,785,984 | 3/1957 | Kenaga | 514/744 |
| 3,576,888 | 4/1971 | Lichstein et al. | 260/633 |
| 3,576,892 | 4/1971 | Ferdinand et al. | 570/214 |
| 3,655,786 | 4/1972 | Gilbert et al. | 570/140 |
| 3,716,591 | 2/1973 | Brandy | 260/649 C |
| 3,810,947 | 5/1974 | Schmerling | 570/193 |
| 4,603,147 | 7/1986 | Peake et al. | 514/744 |

FOREIGN PATENT DOCUMENTS 1034253  6/1966  United Kingdom ................ 514/744

OTHER PUBLICATIONS

Abstract of Japanese Patent J67021-494 (10/24/67).
Abstract of Japanese Patent J 57142-923 (9/3/82).
Tetrahedron Letters 21, 2555–56 (1980).
Abstract of Canadian Patent 1173743-A (9/4/84).
Abstract of Japanese Patent J-56128-701 (10/8/81).

*Primary Examiner*—Allen J. Robinson
*Attorney, Agent, or Firm*—Stanford M. Back; H. Robinson Ertelt; Patrick C. Baker

[57] ABSTRACT

Nematodes and insects are controlled by application of vinyl fluorides of the formula

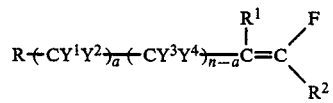

where R is $CH_2X-$, $CHX_2-$, $CX_3-$, $XCH=CH-$, $CH_2=CX-$ or straight chain alkyl($C_2-C_8$);
$R^1$ is hydrogen, fluoro, chloro, bromo, $CH_2Z-$, $CHZ_2-$ or $CZ_3-$;
$R^2$, X and Z independently are hydrogen, fluoro, chloro or bromo; $Y^1$, $Y^2$, $Y^3$, and $Y^4$ independently are $CH_3$ or any value of $R^2$, X and Z; a is 0–12; n is 7–13; and n is greater than a.

Particular species controlled are the root-knot, stunt, lesion, cyst and free-living nematodes, and the southern corn rootworm. The vinyl fluorides also have anthelmintic utility.

7 Claims, No Drawings

VINYL FLUORIDES AND PESTICIDAL USES

This application is a continuation-in-part of application Ser. No. 830,048, filed Feb. 18, 1986 and now abandoned.

TECHNICAL FIELD

This application relates to vinyl fluoride compounds which exhibit biocidal activity, and to methods of use against pests that afflict plants and animals.

The patent and other technical literature describes a variety of unsaturated, halogenated compounds, many of which exhibit pesticidal activity. For example, Japanese patent No. J6 7021-494 discloses as having nematicidal activity, compounds of the formulas $CH_2=CH(CH_2)_xCCl_3$ and $Cl(CH_2)_yHC=CCl_2$ where x is 2 or 4 and y is 1, 3 or 5. U.S. Pat. No. 3,576,888 discloses nematicidal unsaturated fluorinated alcohols and U.S. Pat. No. 3,810,947 describes compounds of the formula

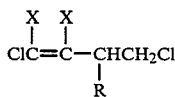

where X is hydrogen and/or chlorine and R is alkyl ($C_1$-$C_{16}$). These compounds are said to be useful as intermediates to insecticides.

Also, U.S. Pat. No. 2,785,984 discloses fumigant nematicidal activity of certain chlorofluoropropenes, such as 1-chloro-1,2,3,3-tetrafluoropropene-1. Various halogenated alkenes and alkynes are known for other than biocidal utility, such as 1,1-difluoro-1-dodecene, described by M. Suda in *Tetrahedron Letters*, 21, 2555-56 (1980) as a reactant with electrophilic reagents such as bromine and Lewis acids. Difluoroethenes are described in Japanese patent No. J5 7142-923 as intermediates in the synthesis of insecticidal acid esters.

Lastly, U.S. Pat. No. 3,576,892 discloses long chain alkyl chlorides in the synthesis of intermediates to nematicides and U.S. Pat. No. 3,716,591 broadly discloses the halogenation with chlorine, bromine or iodine of $C_2$-$C_{50}$ olefins such as 1-octene and 1-nonene and olefins substituted with fluorine. Nematicidal use is an alleged utility, among a variety of uses.

SUMMARY OF THE INVENTION

The biocidal compounds useful in the methods of this invention are vinyl fluorides of the formula (I):

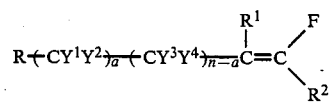

wherein R is $CH_2X-$, $CHX_2-$, $CX_3-$, $XCH=CH-$, $CH_2=CX-$ or straight chain alkyl ($C_2$-$C_8$); $R^1$ is hydrogen, fluoro, chloro, bromo, $CH_2Z-$, $CHZ_2-$ or $CZ_3$; $R^2$, X and Z independently are hydrogen, fluoro, chloro or bromo; $Y^1$, $Y^2$, $Y^3$ and $Y^4$ independently are $CH_3$ or any value of $R^2$, X and Z; a is 0–12; n is 7–13; and n is greater than a.

Vinyl fluorides of formula I exhibit pesticidal utility against helminths that feed upon plants and against other helminths that are indicators of animal anthelmintic activity and therefore are nematicides and anthelmintics for both agricultural and veterinary use. In addition, the vinyl fluorides control soil-borne insects. The biocidal activity of the compounds is surprisingly greater than that of the corresponding allyl compounds.

DETAILED DESCRIPTION

The compounds of formula I may be straight chain or may be branched whereby, for example, when R, $Y^1$, and $Y^2$ are methyl, the compound contains a tertiary carbon atom and is therefore branched. Preferably, however, the carbon atoms of both R and the adjacent $CY^1CY^2$ and $CY^3CY^4$ groups are straight chain. As can be seen from formula I, the vinyl fluorides may contain from 10 to 43 carbon atoms. The halogens in R, $R^1$, Z, X and the Y groups ($Y^1$, $Y^2$, $Y^3$, $Y^4$) may be the same or mixed, and preferably are all fluorine or a mixture of fluorine and chlorine. Preferred classes of the vinyl fluorides are those (1) wherein X and the Y groups are hydrogen, (2) wherein X and the Y groups are hydrogen and $R^2$ is fluoro or chloro, (3) wherein X and the Y groups are hydrogen and $R^1$ is fluoro, chloro or bromo, and (4) wherein X and, the Y groups are hydrogen and $R^2$ is fluoro or chloro. The compounds of formula I include the various isomers and mixtures of isomers.

The vinyl fluorides of formula I are prepared in a generally known manner. When each of $R^1$, X and the Y groups is hydrogen and $R^2$ is halogen, for example, the compounds are prepared by the method of Hayaski et al., *Chemistry Letters*, Chemical Society of Japan, 983–986 (1979), by reacting an aldehyde with the appropriate halogenated methane in the presence of zinc dust and triphenyl phosphine in dimethylacetamide. This procedure is also effective for preparation of vinyl fluorides of formula I wherein X and Y groups are hydrogen, $R^1$ is methyl and $R^2$ is halogen.

To obtain compounds wherein X and Y groups are hydrogen and $R^1$ and $R^2$ are fluorine, the method of Burton and Kehoe, *J. Org. Chem.*, 35, No. 5, 1339-1342 (May 1970), may be used. In this synthesis, the appropriate 1-alkene and polyhalogenated alkane are reacted under pressure in the presence of copper chloride and ethanolamine in 1,1-dimethylethanol to yield the corresponding polyhalogenated alkane addition product. This product is then dehydrohalogenated in the presence of zinc dust in 1-methylethanol to yield the corresponding 1,1,2-trifluoro-4-halo-1-alkene. This alkene may then be dehalogenated by known methods, e.g., by reaction with tri-n-butyltin hydride in the presence of alpha, alpha-azobisisobutyronitrile to obtain the compound of formula I.

Preparation of compounds of formula I wherein $R^1$ and $R^2$ are hydrogen is accomplished by the method of McCarthy et al., *J. Am. Chem. Soc.*, 107, 735-737 (1985). Halogen values for X and the Y groups, including mixed halogens, are obtainable by selection of appropriately halogenated starting materials (such as polyhaloalkylated alkenes in the Burton et al synthesis described above) or by halogenation as a final step in the synthesis.

Various other known methods of halogenation and dehydrohalogenation may be used to prepare other compounds of formula I, as described in Examples 5 and 6 below or as evident to those skilled in the art of organic synthesis.

Further details of synthesis are given in the representative examples below. Table 1 (appended) lists the compounds of the examples along with characterizing data and other compounds of formula I.

EXAMPLE 1

1,1-difluoro-1-tetradecene (Compound 17)

Under a nitrogen atmosphere, a stirred solution of 10.0 grams (0.045 mole) of 90% pure tridecylic aldehyde and 19.0 grams (0.091 mole) of dibromodifluoromethane in 25 ml of dimethylacetamide is cooled to 0° C. and a solution of 23.8 grams (0.091 mole) of triphenylphosphine in 35 ml of dimethylacetamide is slowly added dropwise during a two hour period. Upon completion of addition the reaction mixture is warmed to ambient temperature and stirred for 30 minutes. After this time 5.9 grams (0.091 mole) of zinc dust is cautiously added portionwise. Upon completion of addition, the reaction mixture is heated to 90° C. and stirred for three hours, then cooled to ambient temperature and stirred for 16 hours. The reaction mixture is filtered and the filtrate diluted with water. The mixture is extracted with hexane using a continuous extracting apparatus. The organic layer is concentrated under reduced pressure to a residual oil/solid mixture. The residue is distilled under reduced pressure through a Vigreux column to yield 3.9 grams of 1,1-difluoro-1-tetradecane; b.p. 140°–145° C./35 mm. The nmr spectrum is consistent with the proposed structure. Analysis: calc'd for $C_{14}H_{25}F_2$: C 72.37, H 11.28; Found: C 72.55, H 11.00.

EXAMPLE 2

1,1-difluoro-2-methyl-1-dodecene (Compound 9)

This compound is prepared as in Example 1, using 18.4 grams (0.10 mole) of 2-dodecanone, 42.0 grams (0.20 mole) of dibromodifluoromethane, 52.5 grams (0.20 mole) of triphenylphosphine, and 13.1 grams (0.20 mole) of zinc dust in 135 ml of dimethylacetamide. The yield of 1,1-difluoro-2-methyl-1-dodecene is 1.3 grams; b.p. 59°–62° C./0.6 mm. The nmr spectra are consistent with the proposed structure.

EXAMPLE 3

1-chloro-1-fluoro-1-dodecene (Compound 5)

This compound is prepared as in Example 1, using 9.4 ml (0.045 mole) of undecyclic aldehyde, 12.5 grams (0.091 mole) of trichlorofluoromethane, 23.8 grams (0.091 mole) of triphenylphosphine, and 5.9 grams (0.091 mole) of zinc dust in 60 ml of dimethylacetamide. The yield of 1-chloro-1-fluoro-1-dodecene is 0.8 gram; b.p. 135°–137° C./28 mm. The nmr spectrum is consistent with the proposed structure, and indicates that the product is a 50/50 mixture of cis/trans isomers.

EXAMPLE 4

1,1-difluoro-1,11-dodecadiene (Compound 11)

This compound is prepared as in Example 1, using 41.6 ml (0.2 mole) of 10-undecenal, 83.9 grams (0.4 mole) of dichlorodifluoromethane, 104.9 grams (0.4 mole) of triphenylphosphine, and 26.2 grams (0.4 mole) of zinc dust in 270 ml of dimethylacetamide. The yield of 1,1-difluoro-1,11-dodecadiene is 21.3 grams; b.p. 98°–100° C./25 mm. The nmr spectra are consistent with the proposed structure.

EXAMPLE 5

11,12-dibromo-1,1-difluoro-1-dodecene (Compound 10)

To a stirred solution of 5.0 grams (0.025 mole) of 1,1-difluoro-1,11-dodecadiene (prepared as in Example 4) in 50 ml of carbon tetrachloride is added dropwise a solution of 4.0 grams (0.025 mole) of bromine in 25 ml of carbon tetrachloride during a one hour period. Upon completion of addition, the reaction mixture is stirred at ambient temperature for 18 hours. The reaction mixture is placed in a separatory funnel and washed with water, then with an aqueous sodium chloride solution. The organic layer is dried with magnesium sulfate and filtered. The filtrate is concentrated, then dried under reduced pressure to yield 8.5 grams of 11,12-dibromo-1,1-difluoro-1-dodecene as an oil. The nmr spectra are consistent with the proposed structure. Analysis: calc'd for $C_{12}H_{20}Br_2F_2$: C 39.80, H 5.57; Found: C 39.08, H 5.73.

EXAMPLE 6

11-bromo-1,1-difluoro-1,11-dodecadiene and 12-bromo-1,1-difluoro-1,11-dodecadiene (Compound 13 and Compound 12, respectively)

A sample of 8.0 grams (0.022 mole) of 11,12-dibromo-1,1-difluoro-1-dodecene (prepared as in Example 5) is stirred and 4.9 ml (0.033 mole) of 1,8-diazabicyclo[5.4.0]undec-7-ene (DBU) is added dropwise during a 10–15 minute period. Upon completion of addition, the reaction mixture is allowed to stand at ambient temperature for 60 hours. The reaction mixture is stirred with 35 ml of diethyl ether and filtered. The filter cake is washed with diethyl ether, and the wash and filtrate combined. The combination is washed with three 20 ml portions of water. The organic layer is dried with sodium sulfate and filtered. The filtrate is concentrated under reduced pressure to a residual oil. The oil is fractionally distilled under reduced pressure through a 15 cm Vigreux column. Gas chromatographic analysis of the distillates identifies two fractions, which when combined contain a majority of product. One fraction, b.p. 98° C./1.4 mm, is analyzed by high resolution NMR and found to be 47% 12-bromo-1,1-difluoro-1,11-dodecadiene. The yield is 1.6 grams.

Analysis: calc'd for $C_{12}H_{19}BrF_2$: C 51.26, H 6.81; Found: C 50.97, H 6.75.

A second fraction, b.p. 95°–98° C./1.4 mm, is also analyzed by high resolution NMR and found to be 67% 11-bromo-1,1-difluoro-1,11-dodecadiene. The yield is 2.1 grams. Analysis: calc'd for $C_{12}H_{19}BrF_2$: C 51.26, H 6.81; Found: C 51.43, H 6.60.

EXAMPLE 7

4-chloro-1,1,2-trifluoro-1-dodecene (Compound 18)

(A) a 200 ml pressure bottle is charged with 15.1 ml (0.08 mole) of 1-decene, 19.2 ml (0.16 mole) of 1,1,2-trichloro-2,2,1-trifluoroethane, 0.07 gram (0.0007 mole) of copper (I) chloride and 2.4 ml (0.04 mole) of ethanolamine in 70 ml of 1,1-dimethylethanol. The bottle is sealed, and the reaction mixture heated to 90°–100° C. and stirred for 64 hours. The reaction mixture is cooled to ambient temperature and filtered. The filtrate is concentrated under reduced pressure, and the concentrate diluted with pentane. The mixture is washed with three portions of water, then with an aqueous saturated sodium chloride solution. The organic layer is dried with sodium sulfate and filtered. The filtrate is concentrated under reduced pressure to a residue. The residue is distilled to give 11.4 grams of 1,2,4-trichloro-1,1,2-trifluorododecane; b.p. 70°–72° C./0.025 mm. The nmr spectrum is consistent with the proposed structure.

Analysis: calc'd for $C_{12}H_{20}Cl_3F_3$: C 43.99, H, 6.15; Found: C 44.47, H 6.21.

(B) A stirred suspension of 2.1 grams (0.033 mole) of zinc dust in 100 ml of 1-methylethanol is heated to 100° C. and a solution of 10.0 grams (0.030 mole) of 1,2,4-trichloro-1,1,2-trifluorodedecane in 50 ml of 1-methylethanol is added dropwise. Upon completion of addition, the reaction mixture is heated at 100° C. for 60 hours. The reaction mixture is cooled to ambient temperature and filtered. The filtrate is concentrated under reduced pressure to a residual oil. The oil is fractionally distilled under reduced pressure through a Vigreux column. The appropriate fractions are combined to yield 4.0 grams of 4-chloro-1,1,2-trifluoro-1-dodecene; b.p. 70°–73° C./0.5 mm. The nmr spectrum is consistent with the proposed structure.

EXAMPLE 8

1,1,2-trifluoro-1-dodecene (Compound 8)

A stirred mixture of 4.6 grams (0.0179 mole) of 4-chloro-1,1,2-trifluoro-1-dodecene (prepared as in Example 7) and 0.04 gram (0.0003 mole) of alpha, alpha-azobisisobutyronitrile is flushed with argon and 5.1 ml (0.019 mole) of tri-n-butyltin hydride is added dropwise. Upon completion of addition, the reaction mixture is stirred at ambient temperature for 16 hours. The reaction mixture is fractionally distilled under reduced pressure through a Vigreux column. The appropriate fractions are recombined and redistilled, again under reduced pressure and through a Vigreux column. The yield of 1,1,2-trifluoro-1-dodecene is 1.2 grams; b.p. 42°–45° C./0.45 mm. The nmr spectrum is consistent with the proposed structure. Analysis: calc'd for $C_{12}H_{21}F_3$: C 64.85, H 9.52; Found: C 64.82, H 9.32.

EXAMPLE 9

1,1,13,13,14,14,14-heptafluoro-1-tetradecene (Compound 41)

(A) A pressure bottle equipped with a magnetic stirrer was purged with argon and 25.6 grams (0.15 mole) of 10-undecen-1-ol, then 3.6 grams (0.015 mole) of benzoyl peroxide, followed by 36.9 grams (01.5 mole) of condensed pentafluoroethyl iodide were added. The bottle was sealed and the reaction mixture was heated at 60°–65° C. for 60 hours. The reaction mixture was cooled in a dry ice-acetone bath. The bottle was opened and 125 ml of pentane was added. The mixture was allowed to warm to ambient temperature then was washed with three 40 ml portions of saturated aqueous sodium bicarbonate solution. The organic layer was dried with magnesium sulfate and filtered. The filtrate was concentrated under reduced pressure to a residual oil. The oil was distilled under vacuum (82°–119° C./0.4 mm) to yield 17.1 grams of 10-iodo-12,12,13,13,13-pentafluorotridecanol following combination of the appropriate fractions.

(B) The reaction mixture containing 16.5 grams (0.04 mole) of the 10-iodo-12,12,13,13,13-pentafluorotridecanol of step (A), 2.0 grams of palladium/charcoal catalyst, and 3.3 grams (0.04 mole) of sodium acetate in 100 ml of ethanol was hydrogenated using a Parr hydrogenator. Upon completion of the uptake of the theoretical amount of hydrogen the reaction mixture was concentrated under reduced pressure and stirred with 125 ml of pentane. The mixture was filtered and the filtrate was concentrated under reduced pressure to a residual semi-solid. The residue was distilled under vacuum to yield 6.2 grams of 12,12,13,13,13-pentafluorotridecanol; b.p. 112° C./1.4 mm, which solidified on standing; m.p. 41°–43° C. The NMR spectrum was consistent with the proposed structure.

(C) A stirred solution of 2.7 grams (0.021 mole) of oxalyl chloride in 150 ml of methylene chloride was stirred under an argon atmosphere and cooled to −50° to −60° C. A solution of 3.3 grams (0.042 mole) of dimethylsulfoxide in 30 ml of methylene chloride was added dropwise during a 10–15 minute period. Upon completion of addition the reaction mixture was stirred for two minutes and 5.5 grams (0.019 mole) of 12,12,13,13,13-pentafluorotridecanol of step (B) in 35 ml of methylene chloride was added dropwise during a 15 minute period. Upon completion of addition the reaction mixture was stirred for an additional 15 minutes after which 9.6 grams (0.095 mole) of triethylamine was added dropwise during a five minute period. The reaction mixture temperature was maintained at −50° to −60° C. throughout the additions. The reaction mixture was allowed to warm to ambient temperature at which time 175 ml of water was added. The aqueous layer was separated and extracted with three 40 ml portions of methylene chloride. The extracts were combined with the organic layer from the reaction mixture and the combination was washed with three 40 ml portions of saturated aqueous sodium chloride solution. The organic layer was filtered and the filtrate concentrated under reduced pressure to a residual semi-solid. The residue was stirred with 100 ml of pentane and filtered. The filtrate was concentrated under reduced pressure to yield 4.9 grams of 12,12,13,13,13-pentafluorotridecylic aldehyde as an oil. The NMR spectrum was consistent with the proposed structure.

(D) Under an argon atmosphere a stirred solution of 4.2 grams (0.015 mole) of 12,12,13,13,13-pentafluorotridecylic aldehyde of step (C) and 6.1 grams (0.029 mole) of dibromodifluoromethane was cooled to 0° to −5° C. and a solution of 7.6 grams (0.029 mole) of triphenylphosphine in 45 ml of dimethylacetamide was added dropwise during a 5–10 minute period. Upon completion of addition the reaction mixture was allowed to warm to ambient temperature where it stirred for two hours. A small portion of zinc dust, from a total of 1.9 grams (0.029 mole), was added to the reaction mixture. The reaction mixture was heated gently to 35° C. to initiate the reaction. When the reaction commenced, as evidenced by the increase in reaction mixture temperature above 35° C., the remainder of the 1.9 grams of zinc powder was added portionwise during a 10 minute period. Upon completion of addition the reaction mixture was heated to 85°–90° C. where it stirred vigorously for two hours. The reaction mixture was cooled to ambient temperature and stirred with 50 ml of water for 30 minutes. The mixture was steam distilled using pentane as the extraction solvent. The pentane collected during two hours of distillation was concentrated under reduced pressure to an oil residue. The residue was evacuated then distilled, both under high vacuum, to yield 0.6 gram of 1,1,13,13,14,14,14-heptafluoro-1-tetradecene as an oil. The NMR spectrum was consistent with the proposed structure.

Compounds 29, 40 and 42 (Table 1) were prepared in substantially the same manner as described above for Compound 41.

Pesticidal Use

The vinyl fluorides of the invention can be used against a variety of pests that attack plants and animals, particularly insects and helminths. In agriculture, they are useful as insecticides and nematicides, particularly against soil-borne insects and plant-parasitic nematodes but also against air-borne insects and "free-living" nematodes, i.e., nematodes not dependent on any specific plant or other host. An example of the latter is the microbivorous nematode *Caenorhabditis elegans*. This nematode will feed on bacteria such as *Escherichia coli* and is used as a screen for both agricultural and veterinary nematicides of anthelmintics.

When used as anthelmintics, in veterinary treatments for treatment of infestations of *Ascaris lumbricoides* (roundworm in pigs) for example, the compounds may be administered orally, parenterally or topically either alone but more usually in a pharmaceutically acceptable carrier, to provide an appropriate dosage. Such carriers include one or more of water, gelatine, sugars, starches, organic acids such as stearic or citric acid and salts thereof, talc, vegetable fats or oils, gums, glycols and other excipients, for administration as solids (e.g., tablets or capsules) or liquids (e.g., solutions, suspensions or emulsions). The compositions may also contain preservatives, stabilizers, wetting or emulsifying agents, buffers, salts and other therapeutic agents. The compositions may be formulated by conventional methods to contain about 5 to 95% by weight of the anthelmintic vinyl fluoride, preferably about 25 to 75% by weight. Further guidance to anthelmintic activity, formulations and modes of treatment, utilizing the vinyl fluorides of the invention, is available from publications on the subject, such as the article "Chemotherapeutics, Anthelmintic" in Kirk-Othmer, Encyclopedia of Chemical Technology, Third ed., 5, 451–468, and articles cited therein, and in the patent literature, such as U.S. Pat. No. 3,576,892, col. 3, lines 29–56.

As agricultural pesticides, the nematicides and insecticides of this invention may be applied neat to infestations or to the locus where infestations may occur. However, like most agricultural chemicals, they are more usually not applied full strength, but are formulated with agriculturally acceptable carriers normally employed for facilitating the dispersion of active ingredients, with various additives, and optionally with other active ingredients, recognizing the accepted fact that the formulation and mode of application of a toxicant may affect the activity of the material. The present compounds may be applied, for example, to the soil in which nematode or soil insect control is desired, as granules or powders or liquids, the choice of application varying, of course, with the nematode or soil insect species and environmental factors present at the particular locus of infestation. Thus, the compounds may be formulated as granules of various sizes, as dusts, as wettable powders, as emulsifiable concentrates, as solutions, as dispersions, as controlled release compositions, and the like.

A typical formulation may vary widely in concentration of the active ingredient depending on the particular agent used, the additives and carriers used, other active ingredients, and the desired mode of application. With due consideration of these factors, the active ingredient of a typical formulation may, for example, be suitably present at a concentration of from about 0.5% up to about 99.5% by weight of the formulation. Substantially inactive ingredients such as adjuvants and carriers may comprise from about 99.5% by weight to as low as about 0.5% by weight of the formulation. Surface active agents, if employed in the formulation, may be present at various concentrations, suitably in the range of 1 to 30% by weight. The following description, along with the typical formulations used for the biological testing, will serve to guide the formulator in preparation the most effective formulations. In this specification, "carrier" is intended to mean and include diluents, extenders and other vehicles commonly employed in pesticidal and veterinary formulations to control application rates and dosages.

Dusts are admixtures of the active ingredient with finely divided solid carriers and/or diluents such as talc, natural clays, kieselguhr, pyrophyllite, chalk, diatomaceuous earths, calcium phosphates, calcium and magnesium carbonates, sulfur, lime, flours, and other organic and inorganic solid carriers. These finely divided formulations generally have an average particle size of less than about 45 μm, (No. 325, U.S.A. Standard Sieve Series). In most cases, the active ingredient will be present in dust formulations at a concentration in the range of 1 to 15%, and occasionally from 1% to about 30%, the balance of the composition typically being agriculturally acceptable carrier or diluent.

Wettable powders, also useful formulations for these biocides, are in the form of finely divided particles which disperse readily in water or other liquid vehicles. The wettable powder is ultimately applied to the soil or plant as a dry dust or a dispersion in water or other liquid. Typical carriers for wettable powders include fuller's earth, kaolin clays, silicas, and other highly absorbent or adsorbent inorganic diluents. The concentration of active ingredient in wettable powders is dependent upon physical properties of the active ingredient and the absorbency characteristics of the carrier. Liquids and low melting solids (mp 100° C.) are suitably formulated in the concentration range of 5 to 50% by weight, usually from 10 to 30%; high melting solids (mp 100° C.) are formulated in the range of 5 to 95% by weight, usually 50 to 85%. An agriculturally acceptable carrier or diluent, frequently including a small amount of a surfactant to facilitate wetting, dispersion, and suspension, accounts for the balance of the formulation.

Granules are admixtures of the active ingredients with solids of particle sizes generally in the range of 4.75 mm to 150 μm (No. 4 to No. 100, U.S.A. Standard Sieve Series). Granular formulations may employ hard core materials such as sands and other silicates, mineral carbonates, sulfates or phosphates and the like, or porous cores such as attapulgite clays, fuller's earth, kieselguhr, chalk, diatomaceous earths, ground corn cobs, wood dusts and the like. Impregnating or binding agents such as aliphatic and aromatic petroleum solvents, alcohols, ethers, ketones, esters, vegetable oils, polyvinyl acetates, polyvinyl alcohols, dextrins, sugars and the like are commonly used to aid in coating or impregnating the solid carriers with the active ingredient. Emulsifying agents, wetting agents, dispersing agents, and other additives known in the art may also be added.

A typical granular formulation may suitably contain from about 1% to about 50% by weight active ingredient and 99% to 50% by weight of inert materials.

Microencapsulated or other controlled release formulations may also be used with biocides of this invention for control of nematodes and soil insects.

Emulsifiable concentrates (EC's) are homogeneous liquid compositions, usually containing the active ingredient dissolved in a liquid carrier. Commonly used liquid carriers include xylene, heavy aromatic naphthas, isophorone, and other nonvolatile or slightly volatile organic solvents. For application of the active ingredient, these concentrates are dispersed in water, or other liquid vehicle, forming an emulsion, and are normally applied as a spray to the area to be treated. The concentration of the essential active ingredient in EC's may vary according to the manner in which the composition is to be applied, but, in general, is in the range of 0.5 to 95%, frequently 10 to 80%, by weight of active ingredient, with the remaining 99.5 to 5% being surfactant and liquid carrier.

Those vinyl fluorides of the invention which are solids (most are liquids) may be formulated as flowable compositions. Flowables are similar to EC's except that the solid active ingredient is suspended in a liquid carrier, generally water. Flowables, like EC's, may include a small amount of a surfactant, and contain solid active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in nematicidal formulations include, but are not limited to, the alkyl and alkylaryl sulfonates and sulfates and their sodium salts; alkylamide sulfonates, including fatty methyl taurides; alkylaryl polyether alcohols, sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises about 1 to 15% by weight of the biocidal composition.

Other useful formulations include simple solutions of the active ingredient in a relatively nonvolatile solvent such as corn oil, kerosene, propylene glycol, an alcohol, a ketone or other organic solvent. This type of formulation is particularly useful for ultra low volume application.

The concentration of the biocide in use dilution is normally in the range of about 2% to about 0.1%. Many variations of spraying, dusting, soil-incorporated, and controlled or slow release compositions in the art may be used by substituting or adding a compound of this invention into compositions known or apparent to the art.

Pesticidal compositions of the present invention may be formulated and applied with other suitable active ingredients, including other nematicides, insecticides, acaricides, fungicides, plant regulators, herbicides, fertilizers, or with synergists.

In applying the vinyl fluorides, whether alone or with other agricultural chemicals, an effective biocidal amount must be used. While the application rate will vary widely depending on the choice of compound, the formulation and mode of application, the plant species being protected, the planting density and the pest pressure, a suitable use rate may be in the range of 0.5 to 25 kg/hectare, preferably 1 to about 20 kg/hectare. Trees and vines, for example, may require at least 5 kg/hectare whereas annuals such as corn may require considerably lower rates of application, for example 1 to 5 kg/hectare. The vinyl fluorides are, for the most part, liquids at ambient temperatures and pressures, and therefore can be applied as contact or fumigant pesticides to control soil-borne nematodes and insects.

Biological Testing

The vinyl fluoride compounds of the invention were tested against the soil-borne root-knot nematode (*Meloidogyne incognita*), the stunt nematode (*Tylenchorhynchus claytoni*), the lesion nematode (*Pratylenchus penetrans*), the soybean cyst nematode (*Heterodera glycines*), and the free-living *Caenorhabditis elegans*. In addition, the compounds of the invention were tested as soil insecticides against southern corn rootworm larvae (*Diabrotica undecimpunctata howardi*). For these tests (described below), the vinyl fluorides were formulated as standard suspensions, dusts, emulsifable concentrates, granules, water/acetone solutions, as follows:

| Typical 5% dust | % (wt/wt) |
| --- | --- |
| Test Compound | 5 |
| Base | 95 |
| 96% attaclay | |
| 2% highly purified sodium lignosulfonate (100%) | |
| 2% powdered sodium alkyl-naphthalene sulfonate (75%) | |

| Typical 5% emulsifiable concentrate | % (wt/wt) |
| --- | --- |
| Test Compound | 5.0 |
| Emulsifier A | 4.0 |
| Emulsifier B | 0.4 |
| Emulsifier C | 0.8 |
| Emulsifier D | 1.3 |
| Refined xylene solvent | 88.5 |

Emulsifier A is the anionic calcium salt of dodecylbenzene sulfonate. Emulsifier B is a nonionic 6-molar ethylene oxide condensation product with nonylphenol. Emulsifier C is a nonionic 30-molar ethylene oxide condensation product with nonylphenol. Emulsifier D is a nonionic paste of 100% polyalkylene glycol ether.

| Typical 1% and 5% granular formulations | % (wt/wt) | |
| --- | --- | --- |
| Test Compound | 1 | 5 |
| Attapulgite carrier/diluent | 99 | 95 |

The carrier/diluent is a 20/40 or 60/90 mesh hydrated aluminum magnesium silicate of low volatile matter having 2% free moisture.

| Typical suspension | % (wt/wt) |
| --- | --- |
| Test Compound | 0.2 |
| Dimethylsulfoxide | 99.8 |

| Typical solution | (% wt/wt) |
| --- | --- |
| Test Compound | 0.3 |
| Acetone | 55.9 |
| Water | 43.8 |

1. Free-living Nematode

This in-vitro test using the free-living nematode *Caenorhabditis elegans*, is a modification of the assay developed by Simpkin and Coles, *J. Chem. Tech. Biotechnol*, 31: 66–69 (1981). In this test, nematicidal activity is evaluated by placing a suspension of *C. elegans* nematodes in a medium containing a food source (*E. coli*) and a candidate nematicide at test rates of 5.0–0.156 ppm. One milliliter of a test medium consisting of 5 mg ampicillin, 10,000 units of mycostatin and 10 ml of a dense suspension of *Escherichia coli* per 100 ml of a buffer solution, was pipetted into each well of a 24-well microtiter plate. The candidate nematicide, suspended at the appropriate concentration in dimethylsulfoxide, was added to the wells in 2.5 $\mu$l volumes. Each rate of application was replicated two to three times. After thorough mixing of the contents of each well, 50 to 100 $\mu$l of a nematode suspension in a buffer was added so that each well received 10–15 nematodes. After the nematodes were added, the microtiter plates were incubated at 20° C. for 5–6 days. The effect of the candidate nematicide on the survival and the reproduction of *C. elegans* was then evaluated by comparison of the level of population development in the treated wells with that in untreated wells. Specific effects on population development, such as reduced egg hatch or molting disruption, were noted if they were evident. The test results (Table 2 appended) show that the compounds were very active against *C. elegans*. Compound 7 was one of the most active, providing 58% inhibition of reproduction at the low application rate of 0.156 ppm.

2. Root-knot Nematode

The formulated candidate vinyl fluoride was incorporated at rates varying from 10 to 0.078 ppm in soil previously infested with root-knot nematode eggs and larvae. The treated soil was then placed in 7.6 cm fiber pots. A cucumber or a tomato seedling was planted in each pot. The tests were evaluated approximately two-weeks post-treatment. The results (Table 3 appended) show high activity against this nematode, with Compounds 7 and 17 being the most active at the application rates tested. It is believed that Compound 3 would exhibit activity at higher application rates.

3. Root-knot Nematode-Residual Evaluation

The formulated candidate nematicide was incorporated at rates of 5 or 10 ppm into the soil and the thus treated soil was placed in 7.6 cm fiber pots and stored in a greenhouse. At one, two and four weeks post-treatment, the appropriate number of pots were infested with root-knot nematode eggs and larvae. A cucumber or tomato seedling was planted in each pot. The tests were evaluated approximately two-weeks post-infestation. The results (Table 4 appended) show that Compound 17 provided 99% control, at 10 ppm, for up to 4 weeks post-treatment.

4. Fumigant Evaluation

Soil which had been infested with root-knot nematode larvae was treated with the candidate nematicide at rates of 25 to 2.5 ppm and placed in a closed glass jar for three days. The soil was then removed and placed in four 10.2 cm fiber pots and planted with one tomato or cucumber plant per pot. The tests were evaluated approximately two weeks post-treatment. The results (Table 5 appended) show that Compound 18 was highly active, providing 99% control at 10 ppm.

5. Soil Mobility Evaluation

The formulated nematicide was incorporated at the usual rate of 30 ppm into a pot of root-knot nematode infested soil, the soil being subsequently eluted with 15 cm of water (equivalent to 15 cm of rainfall) into a series of two or more pots of untreated nematode-infested soil. More specifically, the namatode-infested soil was placed in 8 cm plastic pots that contained a 10 cm$^3$ layer of sand over a coarse grain filter paper disc. After filling the pots, a second filter paper disc was placed over the soil. Each treated pot was nested over a series of two or more pots containing untreated nematode-infested soil. The untreated soil pots also contained the sand layer and filter paper discs. Fifteen cm of water was slowly dripped onto the top pots. After water application the pots were allowed to drain for 16–18 hours to remove excess water. The top filter was removed and the pots were planted with a cucumber or tomato seedling. The tests were evaluated approximately two weeks post-planting. The results (Table 6 appended) show that Compounds 7 and 19 have some soil mobility.

6. Effect of Formulation Type

The nematicidal activity of Compound 7 was evaluated in several typical formulations in accordance with the procedure described in test 2 above. The results (Table 7 appended) show that the dust formulation was the most effective, although the other formulations also worked well.

7. Stunt Nematode

Formulated candidate nematicide was incorporated at rates of 2.5 or 5 ppm in soil. The treated soil was placed in 10.2 cm fiber pots and planted with corn seedlings. All pots were then infested with a combination of larvae and adult stunt nematodes. The tests were evaluated approximately four weeks post-infestation. The results (Table 8 appended) show as least 78% control at the application rate of 5 ppm.

8. Lesion Nematode

This test was the same as for the stunt nematode except pea seedlings and 7.6 cm fiber pots were used. Table 9 (appended) shows good control at 5 ppm.

9. Cyst Nematode

The test was the same as for the stunt namatode except soybean seedlings were used. Table 10 (appended) shows excellent control at 5 ppm.

10. Systemic Activity

Tomato plants were grown in 10 cm fiber pots until they had four to six true leaves. Three plants per candidate nematicide were placed on a turntable in a spray hood and sprayed with 50 ml of a water/acetone solution of the appropriate amount of candidate nematicide to provide application rates of 2000 ppm or lower. The soil surface in each pot was covered during spraying. After treatment with the candidate nematicide, the test plants were dried in a lighted drying chamber, then placed in a growth chamber, where they were maintained at 25° C. for three days. The soil of each test plant was inoculated with root-knot nematodes by incorporation of the inoculum into the top of 5 cm of soil. The test plants were returned to the growth chamber where they were maintained for 2-3 weeks prior to evaluation. Table 11 (appended) shows that Compound 2 provided 17% control of the root-knot nematode at 2000 ppm application rate.

11. Southern Corn Rootworm Insecticide Tests

Initial and residual soil insecticidal activity of candidate insecticides were evaluated at rates of 4.0 to 0.06 ppm in soil containing corn sprouts and southern corn rootworm larvae. In the initial test, 5 ml of a 10% acetone/water solution containing the appropriate amount of candidate insecticide was pipetted into 30 grams of air-dried soil in a 3 ounce plastic cup. The treated soil was allowed to stand uncovered in a hood for 30 minutes to evaporate the acetone. The process was duplicated for each rate of application. The dried, treated soil in each cup was thoroughly mixed and two 3-day old corn sprouts and ten early third stage (9-10 days old) southern corn rootwork larvae were placed in each cup. The cups were covered with a plastic lid, placed in a closed plastic bag, then incubated in a holding room at 23°-26° C. for 2 days. After this time, the unaffected larvae were extracted from the soil and percent mortality determined. $LC_{50}$ values were determined from percent mortality using probit analysis.

The residual activity of the candidate insecticide in the soil was tested in the same manner as the initial assay except the soil, treated with 4 ppm of candidate insecticide, was infested at 7, 14, 28, and 42 days post-treatment. Candidate insecticides not showing any 7-day residual activity were not tested further.

Table 12 (appended) shows that all of the compounds tested were active as soil insecticides. Compounds 16 and 17 were the most active in the initial tests, providing 95% and 100% kills, respectively, at 0.5 ppm application rate.

TABLE 1

$$R(CY^1Y^2)_{\overline{a}}(CY^3Y^4)_{\overline{n-a}}\overset{R^1}{\underset{}{C}}=C\overset{F}{\underset{R^2}{}}$$

| Cmpd. No. | R | $R^1$ | $R^2$ | $Y^1$ | $Y^2$ | $Y^3$ | $Y^4$ | a | n | b.p. °C./mm Hg |
|---|---|---|---|---|---|---|---|---|---|---|
| 1 | $CH_3$ | H | F | H | H | H | H | 6 | 7 | 96°/74 mm |
| 2 | $CH_3$ | H | F | H | H | H | H | 7 | 8 | 95-97°/27 mm |
| 3 | $CH_3$ | $CH_3$ | F | H | H | H | H | 7 | 8 | 115-116°/32 mm |
| 4 | $CH_3$ | H | H | H | H | H | H | 8 | 9 | 90-94°/10 mm |
| (40/60-cis/trans) | | | | | | | | | | |
| 5 | $CH_3$ | H | Cl | H | H | H | H | 8 | 9 | 135-137°/28 mm |
| (50/50-cis/trans) | | | | | | | | | | |
| 6 | $CH_3$ | H | Br | H | H | H | H | 8 | 9 | |
| (67/33-cis/trans) | | | | | | | | | | |
| 7 | $CH_3$ | H | F | H | H | H | H | 8 | 9 | 70-80°/12 mm |
| 8 | $CH_3$ | F | F | H | H | H | H | 8 | 9 | 42-45°/0.45 mm |
| 9 | $CH_3$ | $CH_3$ | F | H | H | H | H | 8 | 9 | 59-62°/0.6 mm |
| 10 | $CH_2Br$ | H | F | Br | H | H | H | 8 | 9 | |
| 11 | $CH=CH_2$ | H | F | H | H | H | H | 7 | 8 | 98-100°/25 mm |
| 12 | $CH=CHBr$ | H | F | H | H | H | H | 7 | 8 | 98°/1.4 mm |
| (47% plus isomers) | | | | | | | | | | |
| 13 | $CBr=CH_2$ | H | F | H | H | H | H | 7 | 8 | 95-98°/0.4 mm |
| (67% plus isomers) | | | | | | | | | | |
| 14 | $CH=CHBr$ (35%) | Br | F | H | H | H | H | 7 | 8 | 102-104°/0.4 mm |
| | $CBr=CH_2$ (65%) | Br | F | H | H | H | H | 7 | 8 | |
| 15 | $CH_3$ | H | H | H | H | H | H | 9 | 10 | 107°/9.5 mm |
| (37/63-cis/trans) | | | | | | | | | | |
| 16 | $CH_3$ | H | F | H | H | H | H | 9 | 10 | 128°/32 mm |
| 17 | $CH_3$ | H | F | H | H | H | H | 10 | 11 | 144-145°/35 mm |
| 18 | $CH_3(CH_2)_7$ | F | F | H | Cl | H | H | 1 | 2 | 70-73°/0.5 mm |
| 19 | $CH_2Cl$ | H | F | Cl | H | H | H | 1 | 9 | 92-95°/0.4 mm |
| 20 | $CH_3$ | $CF_3$ | F | H | H | H | H | 8 | 9 | 115-118°/30 mm |
| 21 | $CH_3$ | $CF_3$ | F | H | H | H | H | 10 | 11 | 55-57°/0.15 mm |
| 22 | $CH_3$ | $CH_2F$ | F | H | H | H | H | 8 | 9 | |
| 23 | $CH_3$ | $CHF_2$ | F | H | H | H | H | 8 | 9 | |
| 24 | $CH_3$ | Br | F | H | H | H | H | 10 | 11 | 103-106°/1.0 mm |
| 25 | $CH_3$ | Cl | F | H | H | H | H | 8 | 9 | 82°/5.8 mm |
| 26 | $CH_3$ | Cl | F | H | H | H | H | 10 | 11 | 100-101°/0.95 mm |
| 27 | $CH_3$ | Br | F | H | H | H | H | 8 | 9 | |
| 28 | $CH_3$ | $CF_2Br$ | F | H | H | H | H | 8 | 9 | |
| 29 | $CF_3$ | H | F | H | H | H | H | 8 | 9 | 94/7.8 mm |
| 30 | $CF_3$ | H | F | F | F | H | H | 1 | 9 | |
| 31 | $CH_3(CH_2)_4$ | H | F | F | F | H | H | 1 | 5 | |
| 32 | $CH_3$ | H | F | $CH_3$ | H | H | H | 1 | 9 | |
| 33 | $CH_3$ | H | F | $CH_3$ | $CH_3$ | H | H | 1 | 9 | |
| 34 | $CH_3$ | H | F | H | F | H | H | 1 | 9 | |
| 35 | $CH_3$ | H | F | H | H | H | F | 8 | 9 | |
| 36 | $CHF_2$ | F | F | F | F | F | F | 6 | 7 | |
| 37 | $CH_3$ | H | F | H | H | $CH_3$ | H | 8 | 9 | |
| 38 | $CH_3$ | H | F | H | H | $CH_3$ | $CH_3$ | 8 | 9 | |
| 39 | $CH_3(CH_2)_7$ | H | F | H | Br | Br | F | 1 | 2 | |
| 40 | $CF_2Cl$ | H | F | H | H | H | H | 8 | 9 | 99-101.5/4 mm |
| 41 | $CF_3$ | H | F | F | F | H | H | 1 | 11 | oil |
| 42 | $CF_2Cl$ | H | F | F | Cl | H | H | 1 | 11 | oil |

TABLE 2

Vinyl Fluorides: *C. Elegans* Nematode Control

| Cmpd No. | Rate (ppm) | Percent Inhibition of Reproduction | Percent Mortality |
|---|---|---|---|
| 1 | 2.5 | 100 | 92 |
|  | 1.25 (1) | 100 | 8 |
|  | 0.625 (2) | 67 | 0 |
|  | 0.312 | 0 | 0 |
|  | 0.156 | 0 | 0 |
| 2 | 2.5 | 100 | 75 |
|  | 1.25 | 33 | 0 |
|  | 0.625 | 17 | 0 |
|  | 0.312 | 0 | 0 |
|  | 0.156 | 0 | 0 |
| 3 | 5 (3) | 0 | 0 |
|  | 5 | 100 | 100 |
|  | 2.5 | 100 | 83 |
|  | 1.25 (2) | 83 | 0 |
| 5 | 5 (1) | 100 | 17 |
|  | 2.5 (2) | 75 | 0 |
|  | 1.25 | 17 | 0 |
| 6 | 5 | 100 | 83 |
|  | 2.5 | 100 | 58 |
|  | 1.25 | 42 | 0 |
| 7 | 2.5 | 100 | 75 |
|  | 1.25 (1) | 100 | 33 |
|  | 0.625 (1) | 100 | 0 |
|  | 0.312 | 92 | 0 |
|  | 0.156 | 58 | 0 |
| 9 | 5 (1) | 100 | 0 |
|  | 2.5 (1) | 100 | 0 |
|  | 1.25 (1) | 100 | 0 |
| 10 | 5 | 100 | 67 |
|  | 2.5 | 100 | 50 |
|  | 1.25 | 75 | 0 |
| 11 | 5 | 100 | 83 |
|  | 2.5 (1) | 100 | 0 |
|  | 1.25 | 50 | 0 |
| 15 | 5 (1) | 100 | 0 |
|  | 2.5 (2) | 83 | 0 |
|  | 1.25 | 8 | 0 |
| 16 | 2.5 | 25 | 0 |
|  | 1.25 | 8 | 0 |
|  | 0.625 | 0 | 0 |
|  | 0.312 | 0 | 0 |
|  | 0.156 | 0 | 0 |
| 17 | 2.5 (1) | 100 | 0 |
|  | 1.25 | 100 | 0 |
|  | 0.625 | 100 | 0 |
|  | 0.312 | 92 | 0 |
|  | 0.156 | 0 | 0 |

(1) Prevented egg hatch.
(2) Reduced egg hatch.
(3) Preliminary screen.

TABLE 3

Vinyl Fluorides: Root-Knot Nematode Control

| Cmpd. No. | Rate (ppm) | Percent Control |
|---|---|---|
| 1 | 2.5 | 64 |
|  | 1.25 | 25 |
|  | .625 | 0 |
|  | .312 | 0 |
| 2 | 2.5 | 13 |
|  | 1.25 | 0 |
|  | .625 | 0 |
|  | .312 | 0 |
| 3 | 10 | 0 |
| 6 | 10 | 0 |
| 7 | 10 | 100 |
|  | 10 | 95 |
|  | 5 | 95 |
|  | 2.5 | 84 |
|  | 5 | 95 |
|  | 2.5 | 95 |
|  | 1.25 | 95 |
|  | .625 | 84 |
|  | 2.5 | 97 |
|  | 1.25 | 95 |
|  | .625 | 84 |
|  | .312 | 38 |
|  | 2.5 | 99 |
|  | 1.25 | 100 |
|  | .625 | 84 |
|  | .312 | 71 |
| 8 | 10 | 97 |
|  | 10 | 13 |
|  | 5 | 0 |
|  | 2.5 | 0 |
| 9 | 5 | 98 |
|  | 2.5 | 95 |
|  | 10 | 99 |
|  | 5 | 98 |
|  | 2.5 | 82 |
| 10 | 2.5 | 98 |
|  | 1.25 | 19 |
|  | .625 | 6 |
|  | .312 | 0 |
| 11 | 2.5 | 6 |
|  | 1.25 | 0 |
|  | .625 | 0 |
|  | .312 | 0 |
| 16 | 2.5 | 95 |
|  | 1.25 | 50 |
|  | .625 | 13 |
|  | .312 | 0 |
| 17 | 2.5 | 81 |
|  | 1.25 | 96 |
|  | .625 | 97 |
|  | .312 | 97 |
|  | .625 | 97 |
|  | .312 | 97 |
|  | .156 | 63 |
|  | .078 | 13 |
| 18 | 5 | 84 |
|  | 2.5 | 17 |
|  | 10 | 86 |
|  | 5 | 38 |
|  | 2.5 | 0 |
| 19 | 10 | 100 |
|  | 5 | 99 |
|  | 2.5 | 84 |
| 29 | 10 | 99 |
|  | 5 | 75 |
|  | 1.25 | 0 |
|  | .625 | 0 |
| 40 | 10 | 99 |
|  | 5 | 98 |
|  | 1.25 | 50 |
|  | .625 | 44 |
| 42 | 5 | 98 |
|  | 1.25 | 85 |
|  | .625 | 44 |
|  | 10 | 50 |

TABLE 4

Vinyl Fluorides: Root-Knot Nematode Control

| Cmpd. No. | Formulation Type | Rate (ppm) | Inoculation Post-Treatment | Percent Control |
|---|---|---|---|---|
| 7 | 5% Dust | 10 | 1 Week | 81 |
|  |  | 10 | 2 Weeks | 13 |
|  |  | 10 | 4 Weeks | 0 |
| 17 | 5% Dust | 10 | 1 Week | 98 |
|  |  |  | 2 Weeks | 99 |
|  |  |  | 4 Weeks | 99 |

TABLE 5

Vinyl Fluorides: Root-Knot Nematode Fumigant Control

| Cmpd. No. | Rate (ppm) | Percent Control |
|---|---|---|
| 4 | 10 | 0 |
| 5 | 10 | 70 |

TABLE 5-continued
Vinyl Fluorides: Root-Knot Nematode Fumigant Control

| Cmpd. No. | Rate (ppm) | Percent Control |
|---|---|---|
| 15 | 10 | 0 |
| 18 | 10 | 83 |
|  | 10 | 99 |
|  | 5 | 97 |
|  | 10 | 99 |
|  | 5 | 81 |
| 7 | 5 | 100 |
|  | 5 | 81 |
|  | 5 | 100 |
|  | 5 | 100 |
| 29 | 5 | 97 |
|  | 5 | 96 |
|  | 5 | 78 |
|  | 2.5 | 95 |
|  | 2.5 | 50 |
| 40 | 5 | 100 |
|  | 5 | 100 |
|  | 5 | 100 |
|  | 5 | 99 |
|  | 2.5 | 81 |
| 41 | 5 | 99 |
|  | 5 | 99 |
|  | 5 | 99 |
|  | 5 | 95 |

TABLE 6
Vinyl Fluorides: Soil Mobility Against The Root-Knot Nematode

| Cmpd. No. | Location of test Container | Formulation Type | Rate (ppm) | Percent Control |
|---|---|---|---|---|
| 7 | TOP POT | 5% Dust | 30 | 100 |
|  | MID POT |  |  | 13 |
|  | BOT POT |  |  | 17 |
| 17 | TOP POT | 5% Dust | 30 | 98 |
|  | MID POT |  |  | 0 |
|  | BOT POT |  |  | 0 |
| 19 | TOP POT | 5% Dust | 30 | 95 |
|  | MID POT |  |  | 79 |
|  | BOT POT |  |  | 0 |

TABLE 7
Vinyl Fluorides: Formulation Effect In Root-Knot Nematode Control

| Cmpd. No. | Formulation Type | Rate (ppm) | Percent Control |
|---|---|---|---|
| 7 | 1% Granular | 2.5 | 99 |
|  |  | 1.25 | 95 |
|  |  | .625 | 81 |
|  |  | .312 | 25 |
|  | 5% Dust | 2.5 | 99 |
|  |  | 1.25 | 97 |
|  |  | .625 | 97 |
|  |  | .312 | 75 |
|  | 5% EC | 2.5 | 99 |
|  |  | 1.25 | 83 |
|  |  | .625 | 69 |
|  |  | .312 | 19 |
|  | 5% Granular | 2.5 | 84 |
|  |  | 1.25 | 82 |
|  |  | .625 | 25 |
|  |  | .312 | 0 |

TABLE 8
Vinyl Fluorides: Stunt Nematode Control

| Cmpd. No. | Rate (ppm) | Percent Control |
|---|---|---|
| 7 | 5 | 78 |
| 17 | 5 | 81 |

TABLE 9
Vinyl Fluorides: Lesion Nematode Control

| Cmpd. No. | Rate (ppm) | Percent Control |
|---|---|---|
| 7 | 5 | 98 |
| 17 | 5 | 92 |

TABLE 10
Vinyl Fluorides: Cyst Nematode Control

| Cmpd. No. | Rate (ppm) | Percent Control |
|---|---|---|
| 7 | 5 | 99 |
|  | 5 | 96 |
| 17 | 5 | 98 |

TABLE 11
Vinyl Fluorides: Systemic Control of Root-Knot Nematode

| Cmpd. No. | Rate (ppm) | Percent Control |
|---|---|---|
| 2 | 2000 | 17 |
| 7 | 2000 | 0 |
| 16 | 2000 | 0 |
| 17 | 2000 | 0 |
| 18 | 2000 | 0 |
| 5 | 2000 | 0 |

TABLE 12
Vinyl Fluorides: Southern Corn Rootworm Larvae Control

| Cmpd. No. | $LC_{50}$ | Initial Rate | Initial Kill | Residual Rate | Residual % Kill (7-day) |
|---|---|---|---|---|---|
| 1 | 1.678 | 2.00 | 50 |  |  |
|  |  | 1.00 | 30 |  |  |
|  |  | 0.50 | 25 |  |  |
|  |  | 0.25 | 20 |  |  |
|  |  |  |  |  | * |
| 7 | 2.596 | 2.00 | 35 |  |  |
|  |  | 1.00 | 5 |  |  |
|  |  | 0.50 | 0 |  |  |
|  |  | 0.25 | 0 |  |  |
|  |  |  |  | 4.00 | 15 |
| 16 | .144 | 2.00 | 100 |  |  |
|  |  | 1.00 | 100 |  |  |
|  |  | 0.50 | 95 |  |  |
|  |  | 0.25 | 75 |  |  |
|  |  |  |  |  | * |
| 17 | .050 | 1.00 | 100 |  |  |
|  |  | 0.50 | 100 |  |  |
|  |  | 0.25 | 80 |  |  |
|  |  | 0.13 | 75 |  |  |
|  |  | 0.06 | 65 |  |  |
|  |  |  |  | 4.00 | 25 |

*Compound not tested for this residual period.

I claim:

1. A method of controlling nematodes, which comprises applying to the locus where control is desired a nematicidally effective amount of a vinyl fluoride compound selected from the group consisting of $$CH_3(CH_2)_7CH=CF_2,$$
$$CH_3(CH_2)_8CH=CF_2,$$
$$CH_3(CH_2)_9CH=CHF,$$
$$CH_3(CH_2)_9CH=CFCl,$$
$$CH_3(CH_2)_9CH=CFBr,$$
$$CH_3(CH_2)_9CH=CF_2,$$

$$CH_3(CH_2)_9\overset{F}{\underset{|}{C}}=CF_2,$$

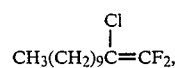

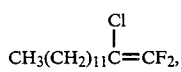

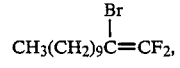

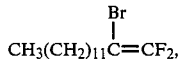

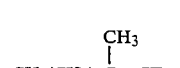

$CH_2BrCHBr(CH_2)_8CH=CF_2,$
$CH_2=CH(CH_2)_8CH=CF_2,$
$BrCH=CH(CH_2)_8CH=CF_2,$
$CH_2=CBr(CH_2)_8CH=CF_2,$

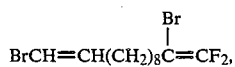

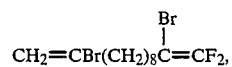

$CH_3(CH_2)_{10}CH=CHF,$
$CH_3(CH_2)_{10}CH=CF_2,$
$CH_3(CH_2)_{11}CH=CF_2,$

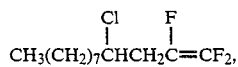

$CH_2ClCHCl(CH_2)_8CH=CF_2,$

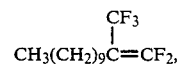

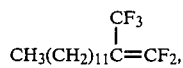

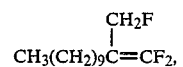

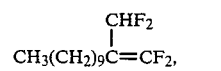

$CF_3CF_2(CH_2)_{10}CH=CF_2$
$ClCF_2(CH_2)_9CH=CF_2$ and
$ClCF_2CFCl(CH_2)_{10}CH=CF_2.$ 2. The method of claim 1 wherein the nematodes are at least one of a root-knot nematode, a stunt nematode, a lesion nematode, a cyst nematode, or a free-living nematode.

3. The method of claim 1 wherein the vinyl fluoride is $CH_3(CH_2)_7CH=CF_2$.

4. The method of claim 1 wherein the vinyl fluoride is

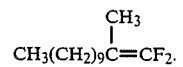

5. The method of claim 1 wherein the vinyl fluoride is $CH_3(CH_2)_9CH=CF_2$.

6. The method of claim 1 wherein the vinyl fluoride is $CH_3(CH_2)_{11}CH=CF_2$.

7. The method of claim 1 wherein the vinyl fluoride is $CH_2ClCHCl(CH_2)_8CH=CF_2$.

* * * * *